United States Patent [19]
Kuczynski et al.

[11] Patent Number: 5,866,164
[45] Date of Patent: Feb. 2, 1999

[54] COMPOSITION AND DOSAGE FORM COMPRISING OPIOID ANTAGONIST

[75] Inventors: Anthony L. Kuczynski, Mountain View; Jerry D. Childers, Sunnyvale; Glen E. Barclay, San Jose; Susan Rodriguez, Stanford; Sonya Merrill, San Jose, all of Calif.

[73] Assignee: ALZA Corporation, Palo Alto, Calif.

[21] Appl. No.: 815,769

[22] Filed: Mar. 12, 1997

Related U.S. Application Data

[60] Provisional application No. 60/013,290 Mar.12, 1996.

[51] Int. Cl.$^6$ ..................................................... A61K 9/42
[52] U.S. Cl. ........................................... 424/472; 424/473
[58] Field of Search ..................................... 424/472, 473

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/260 |
| 4,036,228 | 7/1977 | Theeuwes | 128/260 |
| 4,111,201 | 9/1978 | Theeuwes | 1228/260 |
| 4,111,202 | 9/1978 | Theeuwes | 128/260 |
| 4,327,725 | 5/1982 | Cortese et al. | 128/260 |
| 4,519,801 | 5/1985 | Edgren | 604/892 |
| 4,576,604 | 3/1986 | Guittard et al. | 604/890 |
| 4,612,008 | 9/1986 | Wong et al. | 604/892 |
| 4,844,907 | 7/1989 | Elger et al. | 424/465 |
| 5,021,053 | 6/1991 | Barclay et al. | 604/892.1 |
| 5,198,229 | 3/1993 | Wong et al. | 424/473 |
| 5,312,389 | 5/1994 | Theeuwes et al. | 604/892.1 |
| 5,326,571 | 7/1994 | Wright et al. | 424/473 |
| 5,460,826 | 10/1995 | Merill et al. | 424/470 |
| 5,529,787 | 6/1996 | Merrill et al. | 424/465 |

FOREIGN PATENT DOCUMENTS

| | | |
|---|---|---|
| 0 220 805 A3 | 5/1987 | European Pat. Off. . |
| 0 232 877 A2 | 8/1987 | European Pat. Off. . |
| 2 196 848 | 5/1988 | United Kingdom . |

OTHER PUBLICATIONS

Zenz et al., *Chemical Abstracts*, vol. 122, #142620, 1994.

*Primary Examiner*—Thurman K. Page
*Assistant Examiner*—Kathryne E. Shelborne
*Attorney, Agent, or Firm*—Paul Sabatine; Susan K. Thomas; Michael J. Rafa

[57] ABSTRACT

A composition of matter is disclosed and claimed comprising an opioid antagonist and a high molecular weight poly(alkylene) or a poly(carboxymethylcellulose). A dosage form is disclosed and claimed comprising the composition of matter for displacing an opioid analgesic from the dosage form.

19 Claims, No Drawings

COMPOSITION AND DOSAGE FORM COMPRISING OPIOID ANTAGONIST

This is a provisional application No. 60/013,290, Mar. 12, 1996.

FIELD OF THE INVENTION

This invention pertains to a novel composition comprising an opioid antagonist. This invention also concerns a novel dosage form comprising an opioid antagonist. The invention further concerns a method of administering a dosage form comprising an opioid antagonist for lessening the incidence of drug abuse.

BACKGROUND OF THE INVENTION

Analgesics are drugs which relieve pain and they act to relieve pain by elevating the pain threshold of a patient in need of pain relief. One group of analgesic drugs is the opiates. The opiate group of analgesics is among the most powerfully acting and clinically useful drugs for the relief of pain. The term "opiate" was once used to designate analgesic drugs derived from opium, including morphine, codeine and synthetic congeners of morphine. With the development of totally synthetic drugs with morphine-like actions, the word opioid is used to refer to all drugs, both natural and synthetic, with morphine-like actions. The term "narcotic" as associated with the opioids refers to the physical dependence accompanying the use of these drugs, and with their increasing use it refers to opioid substances that cause dependence.

In addition to their many important medical uses, the opioid drugs are employed commonly for illicit purposes, including emotional, psychological, euphoric, hallucinogenic, depressive and psychedelic experiences. These purposes, and the physical dependence accompanying the administration of these drugs, have led to drug abuse. Drug abuse has become, for many habituates, a way of life. To a rapidly growing segment of the world population use of these drugs is a vogue often seen as fashionable. While these drugs are a necessary part of modern medicine, it would be highly desirable to provide a novel drug delivery system and a novel composition of matter that do not possess drug abuse potential, and thereby seek to lessen the incidence of their abuse and their illicit use.

SUMMARY OF THE INVENTION

In view of the foregoing, it is apparent that a pressing need exists for an improved delivery of opioids for their therapeutic effects, while concomitantly substantially lessening or substantially preventing opioid abuse. Thus, it is an object of this invention to provide a composition of matter indicated for use in a dosage form comprising an abusable opioid, which composition imparts a low potential for abuse of both the composition and the dosage form comprising same. Another object of the invention is to provide a dosage form comprising a first composition containing an opioid and a second composition separate and distinct from the first composition containing an antagonist for lessening opioid abuse.

DETAILED DESCRIPTION OF THE INVENTION

The term "opioid" as used for the purpose of this invention represents an opioid member selected from the group consisting of alfentanil, allylprodine, alphaprodine, apomorphine, anileridine, apocodeine, benzylmorphine, bezitramide, buprenorphine, butorphanol, clonitazene, codeine, cyclorphan, cyprenorphine, desomorphine, dextromoramide, dezocine, diampromide, dihydrocodeine, dehydromorphine, dimenoxadol, eptazocine, ethylmorphine, fentanyl, hydrocodone, hydroxymethylmorphinan, hydromorphone, hydroxypethidine, levophenacylmorphan, levorphanol, lofentanil, methylmorphine, morphine, necomorphine, normethadone, normorphine, opium, oxycodone, oxymorphone, pholcodine, profadol and sufentanil. The opioid can be present as a member selected from the opioid base and the opioid pharmaceutically acceptable salt. The pharmaceutically acceptable salt embraces the inorganic and the organic salt. Representative salts include a member selected from the group consisting of hydrobromide, hydrochloride, mucate, succinate, n-oxide, sulfate, malonate, acetate, phosphate dibasic, phosphate monobasic, acetate trihydrate, bi(heplafluorobutyrate), maleate, bi(methylcarbamate), bi(pentafluoropropionate), mesylate, bi(pyridine-3-carboxylate), bi(trifluoroacetate), bitartrate, chlorhydrate, fumarate and sulfate pentahydrate. The dose of opioid in the first, or opioid composition, is 75 ng to 750mg.

The antagonist present in the second, or antagonist composition, is an effective amount to attenuate, that is to lessen and/or reduce the effect of the opioid present in the first composition. The antagonist is present in 10 ng to 275 mg, or 0.75 to 10 wt %, in the second or antagonist composition that is separate and distinct from the first or opioid composition. The antagonist is an opioid antagonist selected from the group consisting of naltrexone, naloxone, nalmefene, nalide, nalmexone, nalorphine, nalbuphine, nalorphine dinicotinate, present as the pharmaceutically acceptable base and the pharmaceutically acceptable salt thereof.

MODES OF PERFORMING THE INVENTION

EXAMPLE 1

A novel dosage form for delivering hydrocodone to a patient in need of pain relief is prepared as follows: first, 24.8 g of hydrocodone bitartrate hemipentahydrate, 70.3 g of poly(ethylene oxide) of 200,000 average-number molecular weight, available from Union Carbide Institute, West Virginia, and 5.0 mg of hydroxypropylmethylcellulose possessing a 11,200 average-number molecular weight, available from Dow Chemical Co., Midland, Mich., are dry blended for five minutes using a roll mill. Then, 50 ml of denatured ethyl alcohol is added to the dry blend and slowly mixed together for five minutes. After drying at room temperature, the mass is pressed through a 0.0331 inch (0.85 mm) screen and then dried further at room temperature overnight. Next, 0.5 mg of magnesium stearate is blended with the granulation for two minutes to produce a homogenous blend.

Next, a second or antagonist composition is prepared as follows: first, 30.8 g of poly(ethylene oxide) of 7,000,000 weight-average molecular weight, 15.0 g of sodium chloride, 3.0 g of hydroxypropylmethylcellulose of 11,200 number-average molecular weight, 0.4 g of naloxone, and 1.0 g of ferric oxide are blended homogeneously in the presence of denatured alcohol. The homogenous mass is pressed through a 0.0469 inch (1.19 mm) screen and dried overnight at room temperature, and then pressed through a 0.0331 inch (0.85 mm) screen. Then, 1.0 mg of lubricant is added to the granulation. Then, 450 mg of the first composition and 250 mg of the second composition are pressed in a standard tablet press into a bilayered core, with the first composition and the second composition in bilayered arrangement. The bilayered core comprises an oval shape 0.700×0.375 inches (1.78×0.95 cm).

The bilayered core is coated with a semipermeable membrane consisting of 40 mg of cellulose acetate of 39.8% acetyl content and 2 mg of polyethylene glycol of 3,350 viscosity-average molecular weight. The membrane-forming composition is dissolved in acetone:water (95:5 wt:wt), and the wall-forming composition is sprayed around the bilayered core in a coater. Next, two 30 mil (0.762 mm) exit passageways are drilled through the semipermeable membrane to connect the opioid drug layer with the exterior of the dosage form. Finally, the dosage form is dried for 48 hours at 50° F. to remove excess moisture.

EXAMPLE 2

A dosage form is provided by the invention by first preparing a morphine composition, wherein 17.28 g of morphine sulfate pentahydrate, 38.52 g of poly(ethylene oxide) possessing a 200,000 weight-average molecular weight, and 3.60 g of poly(vinyl pyrrolidone) having a number average molecular weight of 40,000, available from ISP Technologies, Texas City, Tex., are added to a planetary mixing bowl. Next, the dry materials are mixed for ten minutes. Then, 16 g of denatured anhydrous ethyl alcohol is slowly added to the blended materials with continuous mixing for 15 minutes. Then, the freshly prepared wet granulation is passed through a 20-mesh screen (0.841 mm sieve opening), allowed to dry at room temperature for 20 hours, and then passed through a 16-mesh screen (1.00 mm sieve opening). Next, the granulation is transferred to a planetary mixer, mixed and lubricated with 0.6 g of magnesium stearate.

Next, a push composition is prepared as follows: first, a binder solution is prepared by dissolving 3 g of hydroxypropylmethylcellulose possessing a number-average molecular weight of 11,200 in 33.7 g of water. Next 0.1 g of butylated hydroxytoluene is dissolved in 2 g of denatured anhydrous alcohol. Approximately 5 g of the hydroxypropylmethylcellulose/water solution is added to the butylated hydroxytoluene/alcohol solution with continuous mixing for two to three minutes. Next, the binder solution preparation is completed by adding the remaining hydroxypropylmethylcellulose/water solution to the butylated hydroxytoluene/alcohol solution, again with continuous mixing thereof.

Next, 36 g of osmagent sodium chloride is sized using a Quadro Co-mil® mill to reduce the particle size of the sodium chloride. Next, 1.2 g of ferric oxide is passed through a 40-mesh screen (0.387 mm opening). Then, the screened materials and 1.2 g of naloxone are added to 75.2 g of pharmaceutically acceptable poly(ethylene oxide) comprising a 7,000,000 weight-average molecular weight and 3 g of hydroxypropylmethylcellulose comprising a number-average molecular weight of 11,200 in a fluid bed granular bowl, and the granulation process is initiated to effect granulation. Next, the dry powders are air suspended and mixed for three minutes. Then, all of the binder solution is sprayed from three nozzles onto the powder. The granulating conditions are monitored during the process. Then, a fluid air mill is used to size the coated granules with an 8-mesh screen (2.38 mm opening screen) and lubricated with 0.28 g of magnesium stearate.

Next, the morphine sulfate pentahydrate composition and the displacement antagonist composition are compressed into a bilayer tablet. First, 434 mg of the morphine sulfate pentahydrate composition is added to the die cavity and compressed. Then, 260 mg of the displacement antagonist composition is added and the layers pressed under a pressure of approximately three tons into a 0.700×0.375 inch (1.78× 0.95 cm) contacting bilayer core, with the antagonist separate from the opioid.

The bilayered core arrangement is coated with a semipermeable wall. The wall-forming composition comprises 95% cellulose acetate having a 39.8% acetyl content, and 5% polyethylene glycol having a 3,350 number-average molecular weight. The semipermeable wall-forming composition is dissolved in an acetone:water (95:5 wt:wt) cosolvent to make a 4% solids solution. The wall-forming composition is sprayed onto and around the bilayer tablets in a coater. Next, two 30-mil (0.762 mm) exit passageways are drilled through the semipermeable wall to connect the opioid-drug layer with the exterior of the dosage system. The residual solvent is removed by drying for 48 hours at 50° C. and 50% humidity. The osmotic dosage forms are dried further for four hours at 50° F. to remove the excess moisture. The dosage form produced by this manufacture comprises in the first composition 28.8% morphine sulfate pentahydrate, 64.2% poly(ethylene oxide) possessing a 200,000 molecular weight, 6% poly(vinyl pyrrolidone) possessing a 40,000 molecular weight, and 1% magnesium stearate. The second composition comprises 62.895% poly(ethylene oxide) comprising a 7,000,000 molecular weight, 30% sodium chloride, 5% hydroxypropylmethylcellulose of 11,200 molecular weight, 0.78% antagonist naloxone, 1% ferric oxide, 0.075% butylated hydroxytoluene, and 0.25% magnesium stearate. The semipermeable wall comprises 95% cellulose acetate comprising a 39.8% acetyl content and 5.0 wt % polyethylene glycol of 3,350 molecular weight. The dosage form comprises two passageways of 30 mil (0.762 mm), and has a morphine sulfate mean release rate of 5 mg/hr.

EXAMPLE 3

A dosage form prepared according to the above example is manufactured and further comprises a wall of 60 to 100 wt % of a cellulose polymer, which polymer comprises a member selected from the group consisting of: a cellulose ester, cellulose diester, cellulose triester, cellulose ether, cellulose ester-ether, cellulose acylate, cellulose diacylate, cellulose triacetate, cellulose acetate, cellulose diacetate, cellulose triacetate, cellulose acetate butyrate, and the like. The wall can also comprise from 0 to 40 wt % of a cellulose ether member selected from the group consisting of: hydroxypropylcellulose, hydroxypropylbutylcellulose and hydroxypropylmethylcellulose, and from 0 to 20 wt % of polyethylene glycol. The total amount of all components comprising the wall is equal to 100 wt %. The wall, in other manufactures, comprises the selectively permeable cellulose ether, ethyl cellulose. The ethyl cellulose comprises an ethoxy group with a degree of substitution (DS) of about 1.4 to 3, equivalent to 40% to 50% ethoxy content, and a viscosity range of 7 to 100 centipoise or higher. More specifically, the wall comprises 40 to 95 wt % ethyl cellulose, from 5 to 60 wt % polyethylene glycol, with the total weight percent of all components comprising the wall equal to 100 wt %. In another manufacture, the wall comprises 45 to 80 wt % of ethylcellulose, from 5 to 30 wt % hydroxypropylcellulose, from 2 to 20 wt % of poly(vinyl pyrrolidone), with the total amount of all components comprising the wall equal to 100 wt %.

EXAMPLE 4

The antagonist composition according to the above examples, wherein the naloxone is replaced by a member selected from the group consisting of: naltrexone, nalmefene, nalide, nalmexone, nalorphine, nalbuphine, nalorphine dinicotinate, and the pharmaceutically acceptable salts thereof.

EXAMPLE 5

In the dosage forms provided by the invention, the first composition can comprises 0.1 to 98 wt % opioid base, opioid salt, or opioid derivative; 10 to 95 wt % poly(alkylene oxide) possessing a 100,000 to 650,000 weight-average molecular weight or 10 to 95 wt % of a carboxymethylcellulose, such as sodium carboxymethylcellulose, lithium carboxymethylcellulose or potassium carboxymethylcellulose possessing a 10,000 to 400,000 molecular weight; 1 to 20 wt % poly(vinyl pyrrolidone) of 40,000 to 75,000 molecular weight, or hydroxypropylcellulose or hydroxypropylmethylcellulose; and 0.10 to 10 wt % lubricant, such as magnesium stearate. In the dosage form, the composition comprising the antagonists comprises 30 to 99 wt % poly(alkylene oxide) exemplified by poly(ethylene oxide) comprising a 3,000,000 to 10,000,000 molecular weight, or 20 to 99 wt % of alkali carboxymethylcellulose comprising a 450,000 to 2,500,000 weight-average molecular weight, available from Aqualon Co., Hopewell, Va.; 0 to 80 wt % of an osmagent, also known as osmotically effective solute, represented by magnesium sulfate, sodium chloride, sodium bicarbonate, sodium succinate, sodium succinate hexahydrate, lithium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, fructose, sodium chloride, fructose, and potassium chloride dextrose; 0.25 to 25 wt % of a hydroxyalkylcellulose selected from the group consisting of hydroxyethylcellulose, hydroxypropylcellulose, hydroxyisopropylcellulose, hydroxybutylcellulose, hydroxypropylmethylcellulose, hydroxypropylethylcellulose, hydroxypropylbutylcellulose, which hydroxyalkylcellulose comprises a 7,500 to 75,000 molecular weight; 0 to 5 wt % ferric oxide; 0 to 3 wt % antioxidant, represented by d-alpha tocopherol, di-alpha tocopherol, d-alpha tocopherol acetate, dl-alpha-tocopherol acetate, d-alpha tocopherol acid succinate, dl-alpha tocopherol acid succinate, ascorbic acid, ascorbyl palmitate, butylated hydroxyanisole, butylated hydroxytoluene and propyl gallate; 0.50 to 10 wt % of an antagonist, selected from the group consisting of naloxone, naltrexone, nalmefene, nalide, nalmexone, nalorphine, nalbuphine, nalorphine dinicotinate, and the pharmaceutically acceptable salts thereof; and 0 to 3 wt % lubricant, represented by magnesium stearate, calcium stearate, corn starch, potato starch, bentonite, citrus pulp and stearic acid; with all ingredients in the push composition equal to 100 wt %.

EXAMPLE 6

The therapeutic composition manufactured by following the above examples and substituting hydromorphone as the opioid provides a hydromorphone drug composition consisting of 1 to 1000 mg of hydromorphone, hydromorphone base, hydromorphone salt, or hydromorphone derivative; at least one of 25 to 500 mg poly(alkylene oxide) of 100,000 to 750,000 molecular weight, or 25 to 500 mg of an alkali carboxymethylcellulose of 10,000 to 300,000 molecular weight; at least one of 1 to 50 mg of poly(vinyl pyrrolidone) of 10,000 to 300,000 molecular weight or 1 to 50 mg of hydroxypropylcellulose or hydroxypropylalkylcellulose of 7,500 to 75,000 molecular weight; 0 to 10 mg of a lubricant, such as magnesium stearate; and 0 to 50 mg of a colorant, such as ferric oxide.

The dosage form provided by the example comprises a push composition that forms a second layer consisting of at least one of 15 to 750 mg of a poly(alkylene oxide) of 3,000,000 to 7,750,000 molecular weight, or 15 to 750 mg of a carboxymethylcellulose, such as sodium carboxymethylcellulose, and potassium carboxymethylcellulose of 450,000 to 2,500,000 molecular weight; 0 to 75 mg of an osmagent, also known as osmotically effective solute, represented by magnesium sulfate, sodium chloride, sodium bicarbonate, sodium succinate, sodium succinate hexahydrate, lithium chloride, potassium sulfate, sodium sulfate, lithium sulfate, potassium acid phosphate, mannitol, urea, inositol, magnesium succinate, tartaric acid, carbohydrates like raffinose, sucrose, glucose, lactose, fructose, sodium chloride, and fructose, potassium chloride and dextrose; 1 to 50 mg of a hydroxyalkylcellulose selected from the group consisting of hydroxyethylcellulose, hydroxypropylcellulose, hydroxyisopropylcellulose, hydroxybutylcellulose, hydroxypropylmethylcellulose, hydroxypropylethylcellulose, hydroxypropylbutylcellulose, which hydroxyalkylcellulose comprises a 7,500 to 75,000 molecular weight; 0 to 10 mg and more preferred 0.05 to 7.5 mg of an antioxidant, represented by d-alpha tocopherol acetate, dl-alpha tocopherol, ascorbyl palmitate, butylated hydroxyanisole, butylated hydroxytoluene and propyl gallate; 0 to 10 mg of a lubricant represented by magnesium stearate, calcium stearate, corn starch, potato starch, bentonite, citrus pulp, and stearic acid; 0 to 10 mg of a colorant; and 0.01 to 20 mg of an antagonist selected from the group consisting of naloxone, naltrexone, nalmefene, nalide, nalmexone, nalorphine and nalbuphine.

EXAMPLE 7

The dosage form further provided by the invention comprises a push displacement composition for pushing the hydromorphone composition from the dosage form, consisting of at least one of 15 to 500 mg of a poly(alkylene oxide) of 3,000,000 to 10,000,000 molecular weight, or 15 to 750 mg of an alkali carboxymethylcellulose, such as sodium carboxymethylcellulose, and potassium carboxymethylcellulose of 450,000 to 2,500,000 molecular weight; 0 to 500 mg and more preferred 5 to 350 mg of an osmagent, also known as osmotically effective solute, represented by magnesium sulfate, sodium chloride, sodium bicarbonate, sodium succinate, sodium succinate hexahydrate, lithium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, fructose, sodium chloride and fructose, potassium chloride and dextrose; 0.01 to 20 mg of an antagonist for an opioid; 1 to 50 mg of a hydroxyalkylcellulose selected from the group consisting of hydroxyethylcellulose, hydroxypropylcellulose, hydroxyisopropylcellulose, hydroxybutylcellulose, hydroxypropylmethylcellulose, hydroxypropylethylcellulose, and hydroxypropylbutylcellulose, which hydroxyalkylcellulose comprises a 7,500 to 75,000 molecular weight; 0 to 10 mg of an antioxidant, represented by d-alpha tocopherol acetate, dl-alpha tocopherol, ascorbyl palmitate, ascorbic acid, butylated hydroxyanisole, butylated hydroxytoluene and propyl gallate; 0 to 10 mg of a lubricant, represented by magnesium stearate, calcium stearate, corn starch, potato starch, bentonite, citrus pulp and stearic acid; and 0 to 10 mg of a colorant.

EXAMPLE 8

A dosage form is prepared as described in Example 2, except no colorant is present in the push composition. Also, rather than two 30-mil exit passageways drilled through the semipermeable wall on the opioid-drug layer, one 30-mil exit passageway is drilled on the opioid-drug layer, and one 30-mil exit passageway is drilled on the push layer.

EXAMPLE 9

A dosage form is prepared as in Example 8, except the poly(ethylene oxide) comprises a 5,000,000 to 15,000,000 weight-average molecular weight in the push composition.

ADDITIONAL DISCLOSURE OF THE INVENTION

The expression "exit means" for the dosage form as used comprises means and methods suitable for the metered release of beneficial drug morphine from the dosage form. The exit means comprises at least one passageway, orifice, or the like, through the wall for communicating with morphine in the dosage form. The expression, "at least one passageway" comprises aperture, orifice, bore, micropore, porous composition, porous element through which the drug can migrate, hollow fiber, capillary tube, porous overlay, porous insert, and the like. The expression also includes a material that erodes or is leached from the wall in the fluid environment of use to produce least one passageway in the dosage form. Representative materials suitable for forming at least one passageway, or a multiplicity of passageways, include an erodible poly(glycolic) acid or poly(lactic) acid member in the wall, a gelatinous filament, poly(vinyl alcohol), leachable materials, such as fluid-removable pore-forming polysaccharides, salts, oxides, or the like. A passageway, or a plurality of passageways, can be formed by leaching a material, such as sorbitol, lactose, fructose, maltose, mannose, glucose, and the like from the wall. The passageway can have any shape, such as round, triangular, square, elliptical, and the like for assisting in the metered release of the opioid-drug from the dosage form. The dosage from can be constructed with one or more passageways in spaced-apart relations, or more than one passageway on a single surface of a dosage form. Passageways and equipment for forming passageways are disclosed in U.S. Pat. Nos. 3,845,770; 3,916,899; 4,063,064 and 4,088,864. Passageways formed by leaching are disclosed in U.S. Pat. Nos. 4,200,098 and 4,285,987.

Exemplary solvents used for the present purpose comprise inorganic and organic solvents that do not adversely harm the materials and the final wall or the final compositions in the dosage form. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclo-hexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DISCLOSURE FOR USING THE INVENTION

The invention concerns a method for administering an opioid analgesic to a patient from a dosage form characterized by a separate composition comprising an antagonist for an opioid to substantially lessen opioid abuse.

The method provides administering 10 ng to 750 mg of an opioid analgesic to the patient from a dosage form comprising a semipermeable wall permeable to aqueous-biological fluid and impervious to an opioid; an opioid composition, which dosage form comprises 10 to 98 wt % opioid, 10 to 80 wt % poly(alkylene oxide) possessing a 100,000 to 650,000 molecular weight, and 1 to 20 wt % poly(vinyl pyrrolidone) of 40,000 to 75,000 molecular weight, and a push-displacement composition comprising 40 to 90 wt % poly(alkylene oxide) comprising a 3,000,000 to 15,000,000 molecular weight, 0 to 80 wt % of an osmagent, and 0.25 to 25 wt % of a hydroxyalkylcellulose possessing a 7,500 to 75,000 molecular weight, and 0.01 to 10% of an antagonist maintained in the antagonist composition; and 0 to 5% of a colorant, which opioid composition and push-displacement compositions are surrounded by the semipermeable wall; and exit means in the wall for delivering the opioid from the dosage form by imbibing fluid through the wall into the dosage form, causing the opioid composition and the push-displacement composition to expand and push the opioid drug composition through the exit means, whereby through the combined operations of the dosage form, the opioid analgesic is delivered at a therapeutically effective dose at a controlled rate over a sustained period of time.

The invention is characterized additionally by the invention's ability to administer an opioid analgesic to a patient in need of an opioid analgesic from a dosage form while simultaneously maintaining an opioid antagonist in the dosage form to prevent opioid abuse. Thus, the dosage form of the present invention provides the following advantages: (1) a therapeutic opioid analgesic effect that is essentially constant; (2) smoothness and consistency in the level of opioid analgesic delivered to the blood of the patient; (3) reduced potential for misuse or abuse of the opioid-containing dosage form; (4) maintains the opioid and antagonist separate in the dosage form; (5) a decrease in the risk of overdosing and resulting toxic reactions; (6) improvement in patient compliance accompanied by a recommended therapy program; (7) elimination of undesirable interactions and reactions between the opioid and the opioid antagonist contained in the dosage form; (8) administration of a drug opioid composition free of an antagonist; and (9) improvement in the treatment of an opioid addict to correctly and safely use opioid maintenance as both clinical inpatient and clinical outpatient treatment.

Inasmuch as the foregoing specification comprises disclosed embodiments, it is understood what variations and modifications may be made herein, in accordance with the principles disclosed, without departing from the invention.

We claim:

1. An osmotic dosage form comprising:
   (a) a wall comprising a semipermeable composition, which wall surrounds:
   (b) a bilayer core comprising:
      (i) a first layer comprising 75 ng to 750 mg of an analgesic opioid;
      (ii) a second push-displacement layer in bilayered contact with the first layer comprising 40 to 99 wt % of a poly(alkylene oxide) possessing a number-average molecular weight to 10,000,000, and 0.25 to 25 wt % of a hydroxyalkylcellulose possessing a number-average molecular weight to 75,000, and wherein the second layer is characterized by comprising 0.75 to 10 wt % of an antagonist selected from the group consisting of naltrexone, naloxone, nalmefene, nalide, nalmexone, nalorphine and nalbuphine; and, (c) an exit in the wall in contact with the first layer comprising the analgesic opioid for the push-displacement layer to push the first layer comprising the analgesic opioid through the exit from the dosage form.

2. The dosage form according to claim 1, wherein the antagonist is present as the pharmaceutically acceptable salt.

3. The dosage form according to claim 1, wherein the second layer comprises an osmagent.

4. The dosage form according to claim 1, wherein the analgesic opioid comprises a member selected from the group consisting of apomorphine, apocodeine, codeine, dihydrocodeine, dihydromorphine, hydrocodone, hydroxymethylmorphinan, hydromorphone, methylmorphine, morphine, normorphine, oxycodone, benzylmorphine and oxymorphone.

5. The dosage form according to claim 1, wherein the analgesic opioid comprises a member selected from the group consisting of alfentanil, fentanyl, lofentanil and sufentanil.

6. The dosage form according to claim 1, wherein the second layer comprises an antioxidant.

7. The dosage form according to claim 1, wherein the first layer comprises a member selected from the group consisting of allylprodine, alphaprodine, anileridine, bezitramide, buprenorphine, butorphanol, clonitazene, cyclorphan, cyprenorphine, desomorphine, dextromoramide, dezocine, diampromide, dimenoxadol, eptazocine, ethylmorphine, hydroxypethidine, levophenacylmorphan, levorphan, necomorphine, normethadone, pholcodine and profadol, and wherein the first layer composition is free of antagonist.

8. An osmotic dosage form comprising:

(a) a wall comprising a semipermeable composition, which wall surrounds:

(b) a bilayer core comprising:

(i) a first layer comprising 75 ng to 750 mg of an analgesic opioid;

(ii) a second push-displacement layer in contact with the first layer comprising 20 to 99 wt % of a poly(carboxymethylcellulose) comprising a number-average molecular weight to 2,500,000; and 0.25 to 25 wt % of a hydroxyalkylcellulose possessing a number-average molecular weight to 75,000, and wherein the second layer is characterized by comprising 0.75 to 10 wt % of an antagonist selected from the group consisting of naltrexone, naloxone, nalmefene, nalide, nalmexone, nalorphine and nalbuphine; and, (c) an exit in the wall in contact with the first layer for releasing the analgesic opioid by the push-displacement layer pushing the analgesic opioid through the exit from the dosage form.

9. The dosage form according to claim 8, wherein the antagonist is present as the pharmaceutically acceptable salt.

10. The dosage form according to claim 8, wherein the analgesic opioid comprises a member selected from the group consisting of apomorphine, apocodeine, codeine, dihydrocodeine, dihydromorphine, hydrocodone, hydroxymethylmorphan, hydromorphone, methylmorphine, morphine, normorphine, oxycodone, benzylmorphine and oxymorphone.

11. The dosage form according to claim 8, wherein the analgesic opioid comprises a member selected from the group consisting of alfentanil, fentanyl, lofentanil and sufentanil.

12. The dosage form according to claim 8, wherein the first layer is a composition comprising a member selected from the group consisting of allylprodine, alphaprodine, anileridine, bezitramide, buprenorphine, butorphanol, clonitazene, cyclorphan, cyprenorphine, desomorphine, dextromoramide, dezocine, diampromide, dimenoxadol, eptazocine, ethylmorphine, hydroxypethidine, levophenacylmorphan, levorphanol, necomorphine, normethadone, pholcodine and profadol, and wherein the first layer composition is free of antagonist and pressed as a tablet.

13. The dosage form according to claim 8, wherein the dosage form comprises a member selected from the group consisting of d-alpha tocopherol acetate, dl-alpha tocopherol, ascorbyl palmitate, ascorbic acid, butylated hydroxyanidate, butylated hydroxytoluene and propylgallate.

14. A composition comprising 10 ng to 275 mg of naloxone and 15 to 750 mg of a poly(alkylene oxide) comprising a molecular weight to 10,000,000.

15. The composition of matter according to claim 14, wherein the naloxone is replaced by a member selected from the group consisting of naltrexone, nalmefene, nalide, nalmexone, nalorphine and nalbuphine, and the composition is compressed into a tablet.

16. A composition comprising 10 ng to 275 mg of naloxone and 15 to 750 mg of a poly(alkylene oxide) comprising a molecular weight to 2,500,000.

17. The composition of matter according to claim 16, wherein the naloxone is replaced by a member selected from the group consisting of naltrexone, nalmefene, nalide, nalmexone, nalorphine and nalbuphine, and wherein the composition is compressed into a tablet.

18. A composition of matter comprising 10 ng to 275 mg of naloxone, 15 to 750 mg of a poly(alkylene oxide) comprising a molecular weight to 10,000,000, 5 to 350 mg of an osmagent, and 0.05 to 7.5 mg of an antioxidant.

19. A composition of matter comprising 10 ng to 275 mg of naloxone, 15 to 750 mg of a poly(carboxymethylcellulose) comprising a molecular weight to 2,500,000, 5 to 350 mg of an osmagent, and 0.05 to 7.5 mg of an antioxidant.

* * * * *